United States Patent
Merrill et al.

(10) Patent No.: US 8,155,745 B1
(45) Date of Patent: Apr. 10, 2012

(54) SYSTEM AND METHOD FOR GAIT REHABILITATION

(75) Inventors: Daniel R. Merrill, Castaic, CA (US); David L. Hankin, Beverly Hills, CA (US); Brian R. Dearden, Pasadena, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 545 days.

(21) Appl. No.: 12/343,883

(22) Filed: Dec. 24, 2008

(51) Int. Cl.
*A61N 1/36* (2006.01)

(52) U.S. Cl. .................................................. 607/49

(58) Field of Classification Search ................ 607/49
See application file for complete search history.

(56) References Cited

U.S. PATENT DOCUMENTS

| 5,358,514 A | 10/1994 | Schulman et al. |
| 6,507,757 B1 | 1/2003 | Swain et al. |
| 2005/0192645 A1* | 9/2005 | Stein et al. .............. 607/49 |

* cited by examiner

*Primary Examiner* — Kennedy Schaetzle
(74) *Attorney, Agent, or Firm* — Gary D. Schnittgrund

(57) ABSTRACT

The invention is a system and a method of enabling a person with one or two prosthetic legs to walk [i.e. be gait enabled] by using an implanted microstimulator that activates hip abduction, using a control unit, external coil, and a foot mounted foot switch.

4 Claims, 2 Drawing Sheets

SYSTEM AND METHOD FOR GAIT REHABILITATION

BACKGROUND OF THE INVENTION

A person with a prosthetic leg has a similar problem to a person who has a dropped foot, being unable to lift the toes clear of the ground during the swing phase of walking. The dropped foot problem has been addressed by functional electrical stimulation (FES).

The first reference to FES is the work by Liberson, et al, "Functional electrotherapy in stimulation of the peroneal nerve synchronized with the swing phase of gait of hemiplegic patients", *Arch Phys. Med. rehabil* 42, 202-205 (1961). At this time electrotherapy was commonplace, but functional electrotherapy was a new concept. Liberson defined it as follows: " . . . to provide the muscles with electrical stimulation so that at the very time of the stimulation the muscle contraction has a functional purpose, either in locomotion or in prehension or in other muscle activity. Functional electrotherapy is a form of replacement therapy in cases where impulses coming from the central nervous system are lacking."

Liberson used a portable stimulator to correct drop foot during walking. A train of pulses of 20-250 µsec duration, frequency 30-100 Hz and maximum peak current 90 mA was applied through conductive rubber electrodes. The negative (active) electrode was placed over the common peroneal nerve below the knee and the large indifferent electrode either on the thigh or on the lower leg. The stimulator was worn in the pocket and a heel switch was used to trigger the stimulus during the swing phase of the gait cycle. The switch was worn on the shoe on the affected side so that the electrical circuit was interrupted during the stance phase, when the weight was on the heel, and allowed to flow when the heel was lifted during the swing phase. Liberson was enthusiastic about the results, reporting that all the subjects experienced considerable improvement in gait. Despite improvements in the apparatus used, the basic idea of FES has remained unchanged. Sixteen papers on the topic published in the period 1960-1977 have been reviewed by J. H. Burridge et al, *Reviews in Clinical Gerontology*, 8, 155-161 (1998).

U.S. Pat. No. 5,643,332 (Stein) also teaches FES and explains that although variants of the technique have been tried and some success has been obtained, the most common appliance fitted to people with foot drop is an ankle-foot orthosis (AFO) which is a plastics brace that fits around the lower leg and holds the foot at close to a 90° angle with respect to the long axis of the leg, and which does not employ electrical stimulation. Stein gives a number of reasons why FES had not replaced the AFO, amongst which is unreliability of the foot switch. In order to overcome this problem, Stein proposes a tilt sensor for measuring the angular position of the lower leg, but he also provides a socket for a hand or foot switch for those patients who cannot use a tilt sensor as there is insufficient tilt of the lower leg. A muscle stimulator for knee stabilization, also based on a tilt switch, is disclosed in U.S. Pat. No. 4,796,631 (Grigoryev). Muscle stimulation for the treatment and prevention of venous thrombosis and pulmonary embolism is disclosed in U.S. Pat. No. 5,358,513 (Powell, et al).

U.S. Pat. No. 6,507,757 (Swain, et al.) discuss a stimulator for stimulating the leg in a patient with drop foot that is controlled by a foot switch. The invention provides a functional electrical stimulator for attachment to the leg that includes electrodes to apply an electrical stimulus, a foot switch for sending foot rise or foot strike, a circuit responsive to the foot switch for generating stimulation pulses.

Footwear with flashing lights controlled by pressure switches is known, see U.S. Pat. Nos. 5,546,681, 5,746,499 and 6,017,128 (L.A. Gear, Inc.), U.S. Pat. No. 5,903,103 (Garner) and U.S. Pat. No. 6,104,140 (Wut).

Gait training for amputees having at least one prosthetic leg requires a different technology to enable foot swing.

GLOSSARY

Terms are to be interpreted within the context of the specification and claims. The following terms of art are defined and shall be interpreted by these definitions. Medical terms that are not defined here shall be defined according to The American Heritage Stedman's Medical Dictionary, Houghton Mifflin, 1995, which is included by reference in its entirety. Terms that are not defined here shall be defined according to definitions from the ASM Metals Reference Book, $3^{rd}$ Edition, 1993, which is included by reference in its entirety.

Biocompatible. The ability of a long-term implantable medical device to perform its intended function, with the desired degree of incorporation in the host, without eliciting any undesirable local or systemic effects in that host. Regulatory agencies require that implanted objects or devices within the human body be biocompatible.

Body. The entire material or physical structure of an organism, especially of a human.

Cavity. The hollow area within the body, such as a sinus cavity, vagina, mouth, anus, or ear.

Hermetic. Completely sealed by fusion, soldering, brazing, etc., especially against the escape or entry of air or gas.

Implant. To embed an object or a device in a body surgically along a surgically created implantation path.

Insert. To place an object or a device into a body cavity.

Microstimulator. An implantable, biocompatible device having dimensions that are less than about 6 mm diameter and 60 mm in length that is capable of sensing or stimulating electrical signals within living tissue.

Noble metal. A metal with marked resistance to chemical reaction,

Subcutaneous. Located, found, or placed just beneath the skin.

Surgery. A procedure involving the cutting or intrusive penetration of body tissue by cutting or penetration and not by inserting an object or a device into a naturally existing body cavity.

Surgical. Of, relating to, or characteristic of surgeons or surgery.

DETAILED DESCRIPTION OF THE INVENTION

Figure 1:
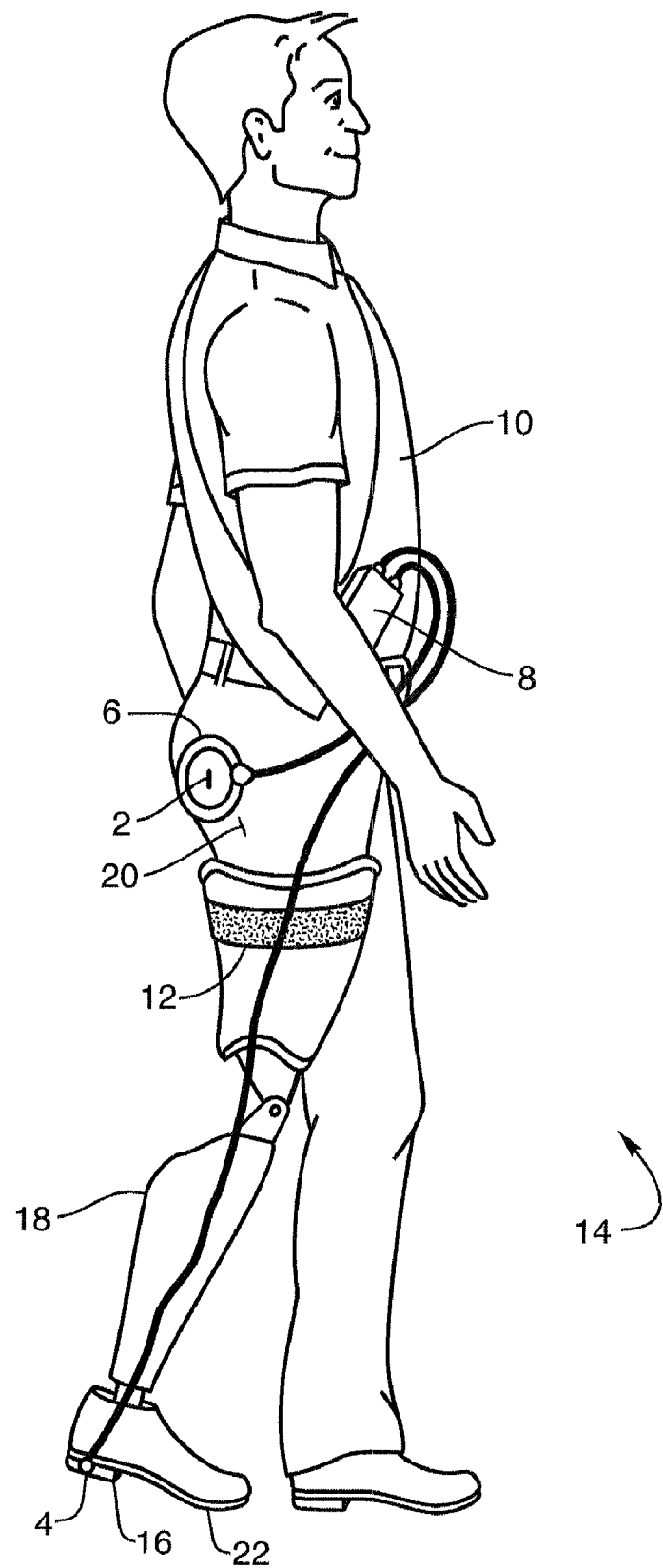
FIG. 1 illustrates a microstimulator based gait rehabilitation system.

A person having a right leg prosthesis 18 is presented in FIG. 1, where in order to enable a more natural gait a gait rehabilitation system 14 is presented which causes stimulation and flexure of the gluteus medius or gluteus maximus muscles 20 at a predetermined point in the gait foot swing, causing hip flexure in the person to slightly raise the prosthetic leg 18 so that the prosthetic foot portion 22 of the leg 18 is raised, thereby avoiding either the need for a wide swing of the leg 18 or dragging of the foot portion 22.

A radio frequency [RF] microstimulator 2 is preferably selected which is hermetic and biocompatible, thus offering no negative reactions and long life when implanted in a hostile living tissue milieu. The RF microstimulator 2 is preferably similar to that described in U.S. Pat. Nos. 5,193,539; 5,193,540; 5,324,316; 5,312,439; and 5,405,367, which are incorporated in their entirety by reference.

In an alternate embodiment, the microstimulator 2 is battery powered, as described in U.S. Pat. Nos. 6,164,284; 6,185, 452; 6,208,894; 6,315,721; 6,564,807; and 7,406,105, incorporated by reference in their entirety. When a battery powered microstimulator is used instead of the RF microstimulator 2, the control unit 8 senses the foot switch 4 through a wireless link, although in an alternate embodiment a wired connection may be employed. The battery powered microstimulator does not employ an external power source during use, thereby eliminating the external coil 6.

The RF microstimulator 2 is preferably implanted in the gluteus medius or in the gluteus maximus muscles 20 of the person, preferably near the superior or inferior gluteal nerves. The microstimulator is supplied electric power and control signals by the external coil 6 that is mounted near the microstimulator 2 but external to the implanted microstimulator 2. It is preferred that the distance between the microstimulator 2 and the external coil 6 is less than about 50 cm.

In an alternate embodiment, the external coil 6 is replaced with an embedded coil 12 that is contained in the prosthetic leg 18. The embedded coil 12 is attached to or built into the prosthetic leg 18. This embedded coil 12 is a solenoid configuration that circumscribes the prosthetic leg 18, as presented in FIG. 1. In alternate embodiments, the embedded coil 12 has a flat pancake or a butterfly morphology. The external coil 6 is preferably applied directly to the person's skin using a temporary adhesive. In an alternate embodiment, the external coil 6 is retained near the implanted microstimulator 2 by a garment that is worn by the person [not illustrated].

The external coil 6 is connected by conductive wire to the control unit 8, which in turn is mounted to a garment 10 that is carried by the person. The control unit 8 is preferably powered by an internal battery pack. In alternate embodiments, the control unit 8 is powered by an external battery pack or by an external AC/DC power supply.

The control unit is connected by wire to a foot switch 4 that is preferably mounted in the heel 16 of the foot portion 22 of the prosthetic leg 18. In an alternate embodiment, the foot switch 4 may be mounted on the foot portion 22 of the prosthetic leg 18. The foot switch 4 contacts the ground and initiates an electrical signal when it is lifted from the ground. This signal activates a control signal from control unit 8 which causes external coil 6 to transmit an RF signal which the microstimulator 2 detects, causing the microstimulator to electrically stimulate the gluteus medius or gluteus maximus muscle, thereby raising the hip of the person and the prosthetic leg 18 and foot 22.

The control unit 8 is programmed so that when the foot switch 4 indicates that the heel has begun to lift off of the ground, the control unit 8 issues commands to the microstimulator 2 to initiate stimulation, causing the desired hip abduction. This stimulation is programmed so that it occurs for a fixed period of time. In an alternate embodiment, the stimulation is programmed to continue until the foot switch 4 indicates that the foot 22 has contacted the ground. After the foot 22 is in contact with the ground, the system resets to the starting condition, ready for another step.

Figure 2:
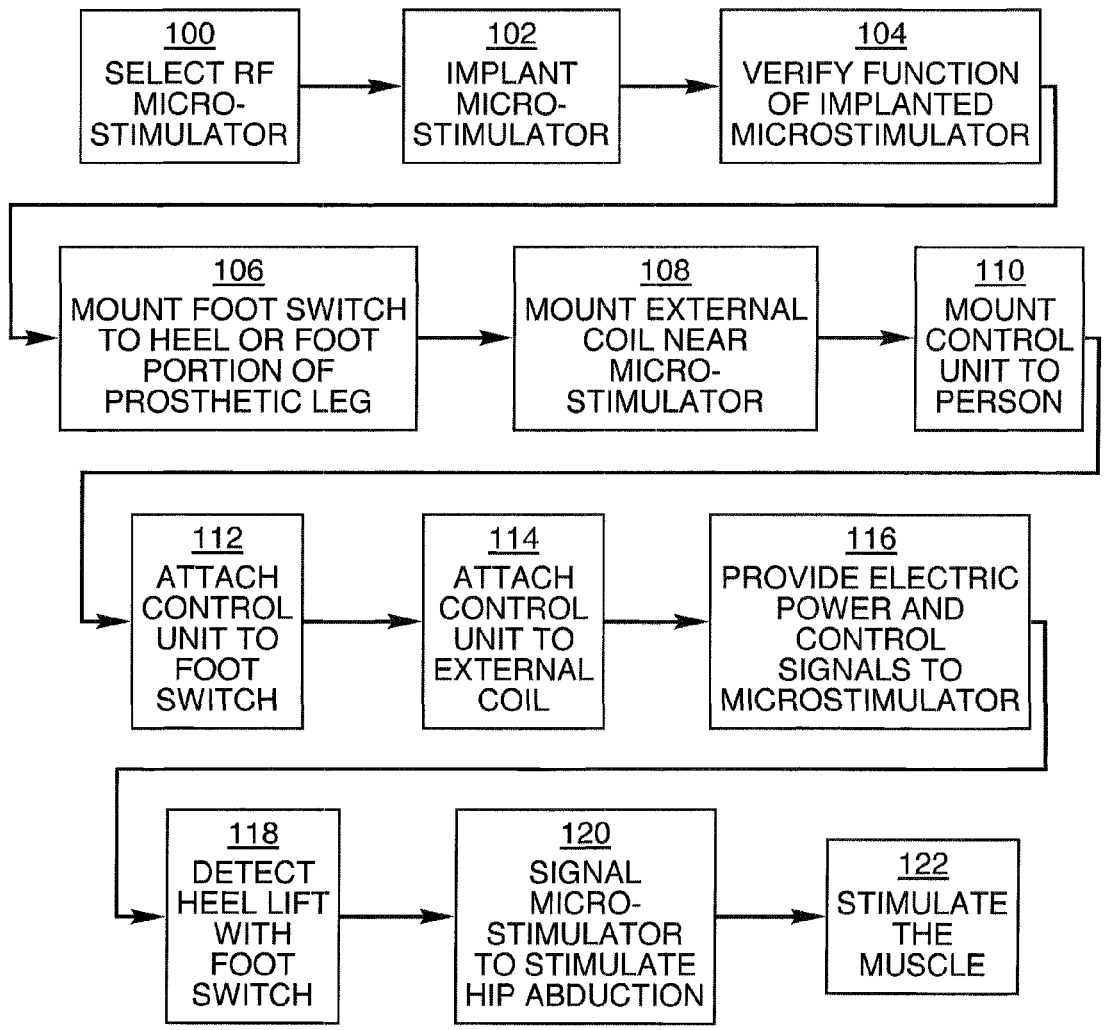
FIG. 2 presents the flow chart for the method of gait rehabilitation.

The method of enabling the gait rehabilitation system 14 is presented in FIG. 2, beginning with step 100, selecting RF microstimulator 2. The RF microstimulator 2 is selected based on its ability to operate for extended periods after implantation in living tissue. It must be biocompatible and hermetically sealed to assure that the living tissue is not harmed by the implanted device.

In step 102, the microstimulator 2 is implanted via minimal surgery into either the gluteus medius or the gluteus maximus 6 near the superior or inferior gluteal nerve.

In step 104 the function of the implanted microstimulator 2 is verified.

In step 106 the foot switch 4 is mounted to the heel 16 or alternately to the foot portion 22 of the prosthetic leg 18.

In step 108 the external coil 6 is mounted near the microstimulator 2.

In step 110 the control unit 8 is mounted to the person.

In step 112 the control unit 8 is attached to the foot switch 4.

In step 114 the control unit 8 is attached to the external coil 6.

In step 116 electric power and control signals are provided to the microstimulator 2.

In step 118 heel lift is detected with the foot switch 4.

In step 120 the microstimulator 2 received an electric signal to stimulate hip abduction in the person.

In step 122 the muscle 20 is stimulated by the implanted microstimulator 2.

The invention claimed is:

1. A method to enable walking by a prosthetic leg fitted person, the prosthetic leg having a foot portion and a heel portion, comprising the steps of:
   selecting a radio frequency powered microstimulator that is suitable for long term, live tissue implantation;
   implanting said microstimulator in the gluteus medius or gluteus maximus;
   mounting an external coil near said microstimulator;
   coupling said microstimulator to said external coil;
   providing electric power and control signals to said microstimulator via said external coil;
   mounting a control unit to the prosthetic fitted person;
   attaching said control unit to a foot switch;
   mounting said foot switch to the heel or foot portion of the prosthetic leg;
   detecting heel lift with said foot switch;
   signaling said microstimulator to initiate hip abduction in the prosthetic leg fitted person; and
   stimulating the muscle with said microstimulator.

2. The method of claim 1, wherein said external coil is a solenoid configuration configured circumferentially around the prosthetic limb.

3. The method of claim 1, wherein said control unit is powered by an internal battery.

4. A gait rehabilitation system for a leg amputee who is fitted with a prosthetic leg which has a foot and a heel portion, comprising:
   a living tissue implantable microstimulator that is configured to be implantable in the gluteus medius or gluteus maximus muscle of the leg amputee;
   an external coil that is mountable external to said implantable microstimulator to provide electrical power and control signals to said implantable microstimulator;
   a foot switch that transmits electrical signals to a control unit, said control unit mountable on the amputee, wherein said control unit processes electrical signals to said external coil;

said foot switch mountable on the heel or foot of the prosthetic leg;

said foot switch configured to detect heel lift and to transmit a signal, when the heel lift is detected, to said mountable control unit; and said implantable microstimulator stimulating hip abduction by activating the implanted gluteus medius or gluteus maximus muscle by electrical stimulation.

* * * * *